United States Patent [19]
Tien et al.

[11] 4,284,771
[45] Aug. 18, 1981

[54] PROCESS FOR PREPARING MELAMINE

[75] Inventors: Hsuan L. Tien, Wayne, N.J.; Kenneth E. Olson, Riverside, Conn.

[73] Assignee: American Cyanamid Company, Stamford, Conn.

[21] Appl. No.: 184,580

[22] Filed: Sep. 8, 1980

[51] Int. Cl.$^3$ ............................................... C07D 251/56
[52] U.S. Cl. ..................................................... 544/200
[58] Field of Search .......................................... 544/200

[56] References Cited

U.S. PATENT DOCUMENTS 2,959,588  11/1960  Williams ............................... 544/200

*Primary Examiner*—John M. Ford
*Attorney, Agent, or Firm*—Harry H. Kline

[57] ABSTRACT

There is provided a novel, economical process for preparing melamine from cyanogen and ammonia in the vapor phase and in the absence of dehydrogenation catalysts.

7 Claims, No Drawings

PROCESS FOR PREPARING MELAMINE

The invention relates to an economical method for the preparation of melamine. More particularly, the invention is directed to the preparation of melamine from cyanogen and ammonia in the vapor phase. Still more particularly, the invention is concerned with the vapor phase reaction of cyanogen and ammonia in the precesnce of alumina, silica or silica-alumina absent dehydrogenation catalysts.

It is well known that melamine can be prepared from the vapor phase reaction of cyanogen and ammonia. However, the presence of a dehydrogenation catalyst such as palladium or platinum, is required for the reaction to proceed. If a process utilizing cyanogen and ammonia could be provided wherein the presence of a dehydrogenation catalyst is not required, a long felt need in the art would be fulfilled.

It is, therefore, a principal object of the invention to provide a novel, economical process for preparing melamine from gaseous reactants, cyanogen and ammonia, in the absence of dehydrogenation catalysts. It is a further object of the invention to provide a reaction in the vapor phase of cyanogen and ammonia in an economical, prompt manner. Other objects and advantages will become apparent from a reading of the ensuing description.

According to the process of the invention, the reaction of ammonia and cyanogen is carried out in a straightforward manner. There are reacted approximately three mols of cyanogen [$(CN)_2$] with three mols of ammonia [$NH_3$] to obtain 1 mol of melamine [$C_3H_6N_6$] and 3 mols of hydrogen cyanide [$HCN$] in good yield and purity.

In general, the aforementioned reaction takes place at atmospheric pressure in the presence of alumina, preferably having a surface area of about 200 $m^2/g$, or silica, preferably having a surface area of about 300 $m^2/g$, or silica-alumina, preferably having a surface area of about 400 $m^2/g$ and an alumina content of 25%. Any temperature sufficient to maintain the vapor phase can be employed, as for instance, at temperatures between about 300° C. and about 600° C. and, preferably, between about 350° C. and 500° C.

Advatageously, the cyanogen and ammonia can be present in almost any mole ratio from 1:1 to 1:20 or even wider. Preferably, however, the ammonia is maintained in excess and mole ratios of ammonia to cyanogen of 4:1 to 10:1 are considered the most practical.

As noted above, the process according to the invention can be carried out with or without a nitrogen gas diluent. If the latter is present a good molar feed ratio may be 7 mols of nitrogen, 10 mols of ammonia and 1 mol of cyanogen to obtain maximum yields.

The time of reaction can vary between about one second and ten seconds, and preferably between three and eight seconds at temperatures ranging between about 350° C. and about 500° C. The invention may be further understood by referring to the examples set forth below which are not intended to limit the invention.

EXAMPLE 1

A quartz tube about 30 in. long and approximately 1 in. in diameter is employed as a reactor. A bed of alumina, having a surface area of 200 $m^2/g$, and being present in a depth of about 8 in. is supported within the reactor on a circular porous quartz plate located at about the midpoint of the tube. The reactor is heated by means of resistance wire wrapping covered by the necessary insulation. Temperatures in the tube and catalyst bed are recorded by means of a sliding iron-constantan thermocouple inserted in a quartz thermowell which extends throughout the catalyst bed.

The gaseous reactants, ammonia and cyanogen, are fed along with nitrogen employing a ratio of $NH_3:(CN)_2:N_2$ at controlled rates of 4:1:7 through flowmeters into a mixer of the cyclone type, then passed from the mixer into the reactor and through the alumina bed heated to about 400° C. contacted for about 3 seconds. The reaction products are then passed into a zone held at about 100° C. for collection of the melamine by desublimation. The residuals are then passed into caustic scrubbers for collection of hydrogen cyanide and unreacted cyanogen.

Melamine present in the crude collected solid product is extracted with hot water and recovered by crystallization from the solution. The melamine product is identified by means of the melting point of its picric acid derivative as well as by its infrared spectra. A 90% yield of theory is attained.

EXAMPLE 2

The procedure of Example 1 above is repeated in every detail except that silica having a surface area of 300 $m^2/g$ is employed in lieu of alumina. A melamine yield of 88% of theory is obtained.

EXAMPLE 3

The procedure of Example 1 above is repeated in every detail except that silica-alumina having a surface area of 400 $m^2/g$ and an alumina content of 25% is employed in lieu of alumina. A melamine yield of 87% of theory is obtained.

EXAMPLE 4

Repeating the procedure of Example 1 in every detail except that nitrogen is omitted, there is obtained an 85% of theory yield of melamine.

We claim:

1. A process for preparing melamine which consists essentially in: reacting cyanogen and ammonia at atmospheric pressure and at a temperature in the range from about 300° C. to about 600° C. in the presence of silica or alumina or silica-alumina and in the presence or absence of nitrogen.

2. The process for preparing melamine according to claim 1 which consists essentially in: reacting cyanogen and ammonia at a temperature in the range from about 300° C. to about 600° C. in the presence of alumina.

3. A process for producing melamine according to claim 1 which consists essentially of reacting cyanogen and a ammonia at a temperature from about 300° C. to about 600° C. in the presence of silica.

4. A process for producing melamine according to claim 1 which consists essentially of reacting cyanogen and ammonia at a temperature from about 300° C. to about 600° C. in the presence of silica-alumina.

5. The process for preparing melamine according to claim 1 which consists essentially in: passing cyanogen and ammonia in a mole ratio of 1:4 to 1:10 through a bed of alumina maintained at a temperature in the range from about 350° C. to about 500 C. and at a contact time of from one to ten seconds.

6. The process for preparing melamine according to claim 1 which consists essentially in: passing cyanogen and ammonia in a mole ratio of 1:4 to 1:10 through a bed of silica maintained at a temperature in the range of about 350° C. to about 500° C. at a contact time of from one to ten seconds.

7. The process for preparing melamine according to claim 1 which consists essentially in: passing cyanogen and ammonia in a mole ratio of 1:4 to 1:10 through a bed of silica-alumina maintained at a temperature in the range of about 350° C. to about 500° C. at a contact time of from one to ten seconds.

* * * * *